US006473634B1

United States Patent
Barni

(10) Patent No.: US 6,473,634 B1
(45) Date of Patent: Oct. 29, 2002

(54) MEDICAL IMAGING AT TWO TEMPORAL RESOLUTIONS FOR TUMOR TREATMENT PLANNING

(75) Inventor: John J. Barni, Mayfield Village, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 111 days.

(21) Appl. No.: 09/718,638

(22) Filed: Nov. 22, 2000

(51) Int. Cl.[7] .............................................. A61B 5/055
(52) U.S. Cl. ........................ 600/425; 382/131; 382/294
(58) Field of Search ................................. 600/425, 410, 600/411, 407, 427; 250/363.04, 363.01; 382/131, 294

(56) References Cited

U.S. PATENT DOCUMENTS 5,974,165 A * 10/1999 Giger et al. ............ 382/294 X
6,076,005 A * 6/2000 Sontag et al. ................ 600/413
6,363,163 B1 * 3/2002 Xu et al. .................. 382/131 X

OTHER PUBLICATIONS

Picker International, Inc., company brochure, 1999.

* cited by examiner

Primary Examiner—Peter Nerbun
(74) Attorney, Agent, or Firm—Fay, Sharpe, Fagan, Minnich & McKee, LLP

(57) ABSTRACT

A method of medical imaging includes obtaining at a first temporal resolution a first medical image 100 of a region of interest of a patient, and obtaining at a second temporal resolution a second medical image 200 of the region of interest. The second temporal resolution is lower than the first temporal resolution. The method also includes registering the first and second medical images with one another such that common reference points in the first and second medical images coincide. Finally, the first and second medical images are superimposed over one another.

20 Claims, 2 Drawing Sheets

MEDICAL IMAGING AT TWO TEMPORAL RESOLUTIONS FOR TUMOR TREATMENT PLANNING

BACKGROUND OF THE INVENTION

The present invention relates to the art of medical imaging. It finds particular application in conjunction with computed tomography (CT), and will be described with particular reference thereto. However, it is to be appreciated that the present invention is also amenable to other like applications and imaging modalities, e.g., magnetic resonance imaging (MRI), single photon emission computed tomography (SPECT), positron emission tomography (PET), fluoroscopy, etc.

Various modalities and types of medical imaging have been found to be useful in the diagnosis of pathology and the planning of therapeutic treatments and surgeries. In particular, conventional modalities of medical imaging (e.g., CT, MRI, SPECT, PET, fluoroscopy, etc.) accord medical professionals the benefit of non-invasive visualization of the patient's anatomy in order to diagnosis conditions and plan treatments.

In an oncological application, for example, medical images are often used to visualize, identify and locate a cancerous tumor. Once identified and located, a medical professional may therapeutically or surgically treat the tumor with guidance from the medical images. Radiotherapy, e.g., involves obliteration of the tumor by delivering an appropriate dose of targeted radiation to the tumor or cancerous tissue. The goal is to completely obliterate the tumor or cancerous tissue while minimizing the radiation received by and/or damage to the surrounding tissue.

High precision image-guided radiotherapy systems have evolved to deliver the desired radiation dose to a desired volume or cross-section. The introduction of multi-leaf collimators (e.g., an 80–100 leaf collimator) on linear accelerators allows the delivery volume or cross-section to be highly spatially resolved. That is, in the planning of the therapy, the radiation delivery area or volume can be made to closely match the size and shape of the cancerous tumor to be obliterated.

While beneficial from the standpoint of accuracy in the radiation delivery, the high precision radiotherapy systems have exposed certain limitations in the medical imaging systems and techniques used to guide the radiotherapy. For example, to accurately and precisely visualize, identify and locate the pathology of interest for diagnosis and therapy planning, typically, a high spatial resolution image(s) of the region including the surrounding anatomy is obtained at high speed. Often, this imaging is carried out some time prior to administering the therapy or treatment. The obtained image(s) generally represents a "still picture" of the patient's anatomy at a particular instant in time, i.e., when the image was obtained.

Unfortunately, at the time of treatment (as opposed to the time of imaging), the tumor to be obliterated, e.g., may have shifted relative to the surrounding anatomy or other reference points. Moreover, administration of the therapy or treatment is not typically instantaneous. That is, the delivery of the targeted radiation, e.g., occurs over time. The treatment or delivery time can be anywhere from 5 to 30 minutes. During this time, the cancerous tumor may be moving relative to the surrounding anatomy or other reference points due to natural biological functions or cycles such as, e.g., respiration, cardiac function, etc. As the tumor moves about, portions thereof will enter and leave the targeted area or volume into which the radiation is being delivered. Accordingly, parts of the tumor may receive less than the planned dose of radiation thereby confounding complete obliteration of the tumor. Additionally, surrounding tissue may be pulled or pushed or otherwise moved by the biological function into the target area or volume and undesirably irradiated and/or damaged.

The present invention contemplates a new and improved planning target volume (PTV) and related technique which overcomes the above-referenced problems and others.

SUMMARY OF THE INVENTION

In accordance with one aspect of the present invention, a method of medical imaging is provided. The method includes obtaining at a first temporal resolution a first medical image of a region of interest of a patient, and obtaining at a second temporal resolution a second medical image of the region of interest. The second temporal resolution is lower than the first temporal resolution. The method also includes registering the first and second medical images with one another such that common reference points in the first and second medical images coincide. Finally, the first and second medical images are superimposed over one another.

In accordance with another aspect of the present invention, a medical imaging apparatus includes a medical imager which produces image representations of a region of interest of a patient at two different temporal resolutions. Registration means align with one another first and second image representations of the same region of interest obtained from the medical imager at different first and second temporal resolutions, respectively. Combining means then superimpose over one another the aligned first and second image representations.

One advantage of the present invention is the ability to visualize, for a targeted tissue mass or tumor, a range or envelope of motion experienced due to normal biological functions.

Another advantage of the present invention is the ability to accurately and precisely visualize the size and/or shape of a targeted tissue mass or tumor.

Yet another advantage of the present invention is relatively improved and flexible treatment planning as compared to previously developed systems and/or techniques.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
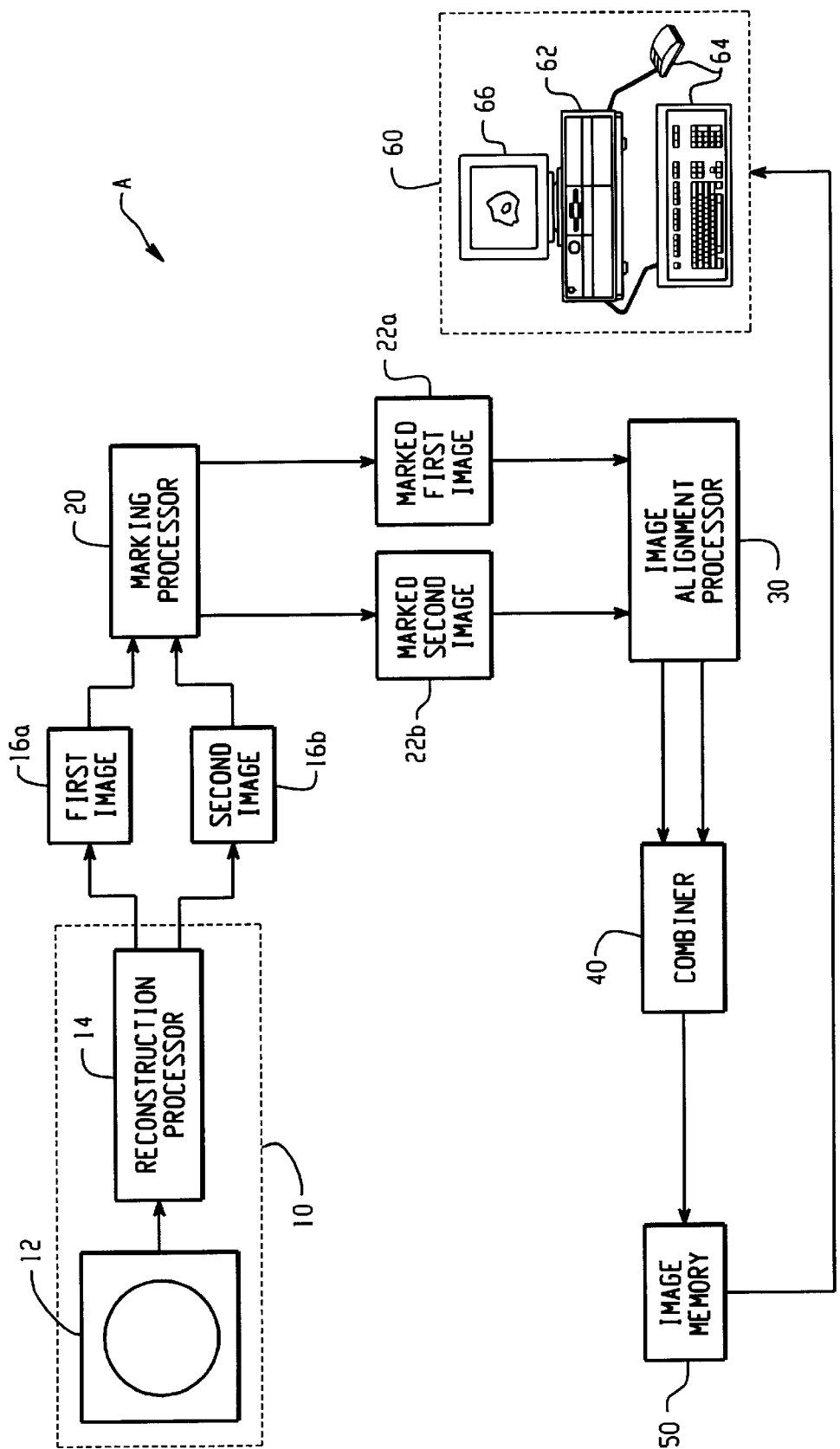
FIG. 1 is a diagrammatic illustration of an exemplary medical imaging and treatment planning system in accordance with aspects of the present invention.

With reference to FIG. 1, an exemplary medical imaging and treatment planning system A includes a medical imaging device or medical imager 10 such as, e.g., a CT scanner, an MRI scanner, a SPECT and/or PET scanner, a fluoroscope, etc. As is known in the art, the medical imager 10 is preferably employed to non-invasively acquire medical images or image representations of a region of interest of a patient positioned therein. Optionally, they are three-dimensional (3D) images or image representations, two-dimensional (2D) cross-sectional slices, surface renderings, or the like. The medical imager 10 preferably includes an imaging apparatus 12 which scans the patient to acquire raw data, and a reconstruction processor 14 which performs or carries out known reconstruction algorithms to reconstruct the images or image representations of the region of interest from the raw data. Depending on the imaging modality, the reconstruction may involve a Fourier transformation, convolution and backprojection, and/or other like reconstruction processes.

In a preferred embodiment, the medical imager 10 selectively produces images at different temporal resolutions. For example, a relatively fast scan produces an image at a higher temporal resolution, while a relatively slow scan produces an image at a lower temporal resolution. Alternately, separate medical imagers 10 are employed to obtain images of the region of interest at a high temporal resolution, and images of the same region of interest at a relatively lower temporal resolution, respectively.

Figures 2, 3:
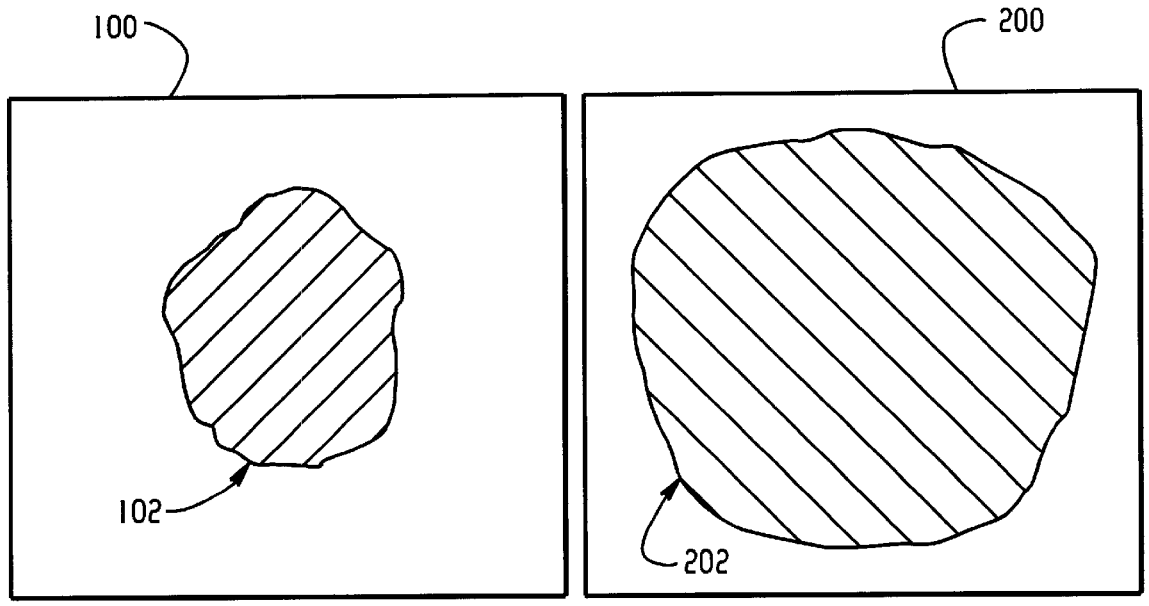
FIG. 2 is a diagrammatic illustration of an exemplary first image obtained at a first temporal resolution with the medical imaging and treatment planning system of FIG. 1 showing a tissue mass.
FIG. 3 is a diagrammatic illustration of an exemplary second image obtained at a second temporal resolution with the medical imaging and treatment planning system of FIG. 1 showing an envelope or range of motion of the tissue mass shown in FIG. 2; and, FIG. 4 is a diagrammatic illustration of an exemplary combined image obtained with the medical imaging and treatment planning system of FIG. 1 showing the image of FIG. 2 overlapped with the image of FIG. 3.

In any event, at least two medical images of the same region of interest are obtained, one at a relatively higher temporal resolution (see, e.g., FIG. 2) and the other at a relatively lower temporal resolution (see, e.g., FIG. 3). Regardless of the order or manner in which the images are obtained, for purposes of distinguishing the images and temporal resolutions herein, the one image along with its corresponding higher temporal resolution are referred to as the first image 100 and the first temporal resolution, and the other image along with its corresponding lower temporal resolution are referred to as the second image 200 and the second temporal resolution. Each of the first and second images are preferably loaded into memories 16a and 16b, respectively, as an array or matrix of image data, e.g., pixel data or voxel data. Alternately, the images may be stored in separate devices (as shown in FIG. 1), or in a common device at distinct locations. Moreover, alternate means of data storage may be employed, e.g., the image data may be stored magnetically, optically, or otherwise.

With respect to the first image 100, preferably the first temporal resolution is sufficiently high such that the reconstructed image may represent the region of interest at a substantially instantaneous point in time. That is, the first image 100 is obtained at a temporal resolution where it may represent a "still picture" or "freeze frame" of the region of interest regardless of anatomical movement therein. The temporal resolution at which the first image 100 is obtain should be high enough that a desired or selected mass of tissue (e.g., a tumor) in the region of interest can be accurately and precisely visualized without blurring from movement caused by, e.g., normal biological functions such as respiration, cardiac functions, etc. In FIG. 2, the image of the tissue mass is labeled with reference numeral 102.

For example, it may be desired that the first image 100 accurately visualize the precise size and shape of a cancerous tumor in the region of interest. However, given a certain amount of movement of the cancerous tumor during the acquisition and/or generation of the image 100, if the first temporal resolution is not sufficiently high, the image of the cancerous tumor 102 may be blurred due to the fact that the image data represents the tumor while it resided in a variety of different locations. Accordingly, the ability to precisely determine the outline (i.e., size and shape) of the tumor is thereby diminished.

The first temporal resolution is optionally achieved by acquiring data rapidly relative to the rate of movement of the tissue mass under consideration. Optionally, the first image 100 may be obtained while the offending biological function is momentarily suspended. For example, where respiration would be otherwise causing the undesired blurring, the first image 100 may be obtained while the patient is holding his breath.

Alternately, as is known in the art, an appropriate gating technique may be used to achieve the first temporal resolution when the offending biological function or movement is cyclical in nature. For example, in prospective applications, the gating is used to trigger data acquisition by the imaging apparatus 12 at the same point in each of a series of consecutive cycles until a enough data is acquired to complete the reconstruction. In this manner, the data is repeatedly captured at the same relative time in each cycle which, e.g., corresponds to a selected phase in the cardiac cycle or the respiratory cycle. In retrospective applications, the data is continuously acquired by the imaging apparatus 12 during multiple cycles, and the gating is used to tag, position a sampling window, or otherwise identify that data which corresponds to data acquired at the same relative time in each cycle. The reconstruction is then carried out using this tagged, sampled or otherwise identified data.

At the second lower temporal resolution, the second image 200 is obtained. As opposed to the first temporal resolution, the second temporal resolution is low, preferably low enough to capture the blurring caused by movement of the tissue mass under consideration. Where the movement experienced is cyclical in nature (as may result from natural biological functions, e.g., respiration, cardiac function, etc.), the data acquisition by the imaging apparatus 12 is preferably carried out over a duration substantially equal to or greater than the period of the cycle. In this manner, the second image 200 visualizes a range or envelope of movement or motion for the tissue mass (e.g., a tumor). That is, given a certain amount of movement of the tissue mass or tumor during the acquisition and/or generation of the image 200, if the second temporal resolution is sufficiently low, the image of the tumor may be blurred due to the fact that the image data represents the tumor while it resided in a variety of different locations. Accordingly, the blurred image 202 of the tumor or tissue mass represents an envelope inside which the tumor or tissue mass is most likely to be found at any given moment. In other words, the blurred image 202 represents the range of motion to which the tissue mass is substantially confined.

In one preferred embodiment, a set of data is continuously acquired by the imaging apparatus 12 while the tissue mass under consideration experiences movement. This same set of data can then be used to reconstruct both the first and second images. Via retrospective gating of the acquired data set, the first image 100 is generated at a high temporal resolution, and the low temporal resolution second image 200 is generated by reconstructing the complete set of data. In an alternate embodiment, the second low temporal resolution image 200 is achieved by averaging together or otherwise combining multiple high temporal resolution images obtained at various times, i.e., when the tissue mass under consideration is in a plurality of different locations.

In any event, the first and second images are selectively marked by a marking engine or marking processor 20. The marking processor 20 preferably colors or otherwise marks the images to enhance visualization of selected anatomical features or other image details. In a preferred embodiment, the visualized tissue mass under consideration in the first image 100 is colored with a first color, and the visualized envelope or range of motion in the second image 200 is colored with a second color different than the first. Alternately, the marking processor 20 automatically marks the images in response to an operator's selection of the anatomical feature or image detail to be marked, or the marking processor 20 enables manual marking of the image by the operator.

In a preferred embodiment, the marked first and second images are loaded from the marking processor 20 into memories 22a and 22b, respectively, as an array or matrix of image data with appropriate marking or coloring. Again, the images may be stored in separate devices (as shown in FIG. 1), or in a common device at distinct locations, and alternate means of data storage may be employed, e.g., the image data may be stored magnetically, optically, or otherwise. Optionally, the marked images are returned to the memories 16a and 16b.

The first and second images are aligned or registered with one another by an image alignment processor 30 such that common reference points in the first and second images coincide. That is, the alignment processor 30 carries out relative translations and/or rotations of the images in order to attain registration of the common reference points in both images. The references points are preferably readily identifiable well defined anatomical landmarks which experience little to no movement or relative displacement with respect to one another from the first image to the second image. For example, the reference points may be the tips of bones which are substantially stationary in view of, or relative to, the movement experienced by the tissue mass under consideration. Optionally, fiducials or other like artificial landmarks which can be visualized in the images are applied during imaging and used as the reference points for alignment purposes.

In a preferred embodiment, the alignment processor 30 automatically registers the images in response to the operator's selection of the reference points in each image. Alternately, the alignment processor 30 enables manual registering of the images by the operator. In either case, the alignment may take place after the images have been marked (as shown in FIG. 1), or prior to the marking.

Figure 4:
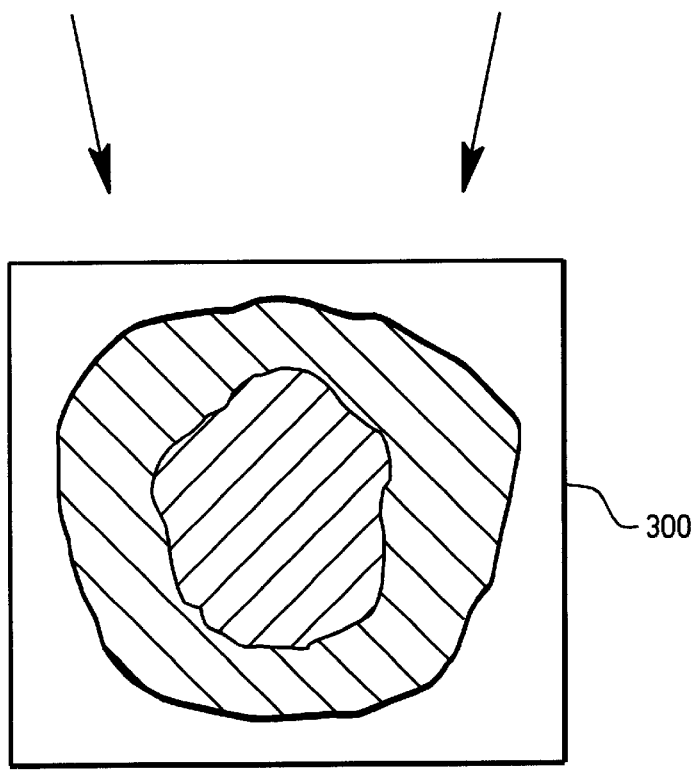

An image combiner 40 superimposes the aligned first and second medical images over one another (see, e.g., FIG. 4). In a preferred embodiment, the combination involves an optionally weighted addition and/or subtraction of the image data on a pixel-by-pixel or voxel-by-voxel basis. Alternately, other image combination and/or superimposing techniques and algorithms, as are known in the art, may be employed by the image combiner 40. In this manner, the combined or superimposed image 300 preferably visualizes both: (i) the precise size and shape of the tissue mass under consideration (i.e., from the first image 100); and, (ii) the range of motion of the tissue mass or the envelope in which the tissue mass resides (i.e., from the second image 200).

The combined or superimposed image 300 from the combiner 40 is loaded into an image memory 50 (or like electronic, magnetic, optical, or other storage device) where it may be selectively accessed by a treatment planning workstation 60. The treatment planning workstation 60 preferably includes a microprocessor or computer 62, one or more input devices 64 (e.g., a computer keyboard, mouse, etc.), and a display device or rendering engine, e.g., a monitor 66. Optionally, the image memory 50 is incorporated in the workstation 60. Likewise, any or all of the aforementioned memories 16 and 22 and processors 14, 20, 30 and 40 may be optionally incorporated in the workstation 60. Alternately, the processors and/or the functions they perform are implemented via hardware configurations, software configurations or combinations of both. In one embodiment, dedicated processors are employed, and in alternate embodiments the microprocessor or computer 62 carries out their respective operations.

In any event, via the input devices 64, an operator (e.g., an oncologist or other medical or technical personnel) can selectively control the treatment planning workstation 60 and/or the entire system A. To provide human-viewable depictions (e.g., 3D representations, 2D cross-sections, surface rendering, etc.) of the combined image 300, the image data in image memory 50 is accessed by the workstation 60 and appropriately formatted for display on the monitor 66. Preferably, both the tissue mass from the first image 100, and the envelope from the second image 200 are visualized in the depiction, optionally, in different colors.

In a preferred embodiment, the workstation 60 is set up for treatment planning. That is, using the combined image 300, treatments such as radiotherapy are simulated on the computer 62 with the results being displayed on the monitor 66.

For example, in one simulation, various doses of radiation are scheduled for delivery to selected regions in the combined image 300. The simulation allows the operator to plan the treatment and review simulated results prior to actual implementation on the patient. A first dose may be scheduled for the region or volume corresponding to the tissue mass. This is nominally termed the high resolution target volume (HI-RES TV). The tissue mass or tumor is precisely visualized in the combined image 300 as a result of the first image 100 being obtained at a high temporal resolution, and the HI-RES TV can be made to accurately conform thereto. Consequently, the first dose delivery is accurately simulated in the planning, and can be accurately performed on the patient. Likewise, a second dose may be scheduled for the region or volume corresponding to the envelope minus the region corresponding to the tissue mass or tumor. This is nominally termed the planning target volume (PTV). The envelope is also visualized in the combined image 300 as a result of the second image 200 being obtained at a low temporal resolution, and the PTV can therefore be made to accurately conform thereto. Consequently, the second dose delivery is accurately simulated in the planning, and can be accurately performed on the patient.

In this manner, greater flexibility and accuracy is achieved in treatment planning to the extent that the precise size and shape of the tumor is readily observable and its range of motion is also readily observable. That is, different doses may be scheduled to achieve different desired results in different regions. For example, a first dose sufficient for obliteration may be scheduled for the entire envelope to ensure that the tumor is destroyed regardless of its movement. Alternately, a first dose may be restricted to the HI-RES TV and a secondary lower dose may be scheduled for the PTV to protect the tissue surrounding the tumor from harm. Numerous variations of the dosage scheduling may be simulated and applied to the patient to test and achieve particular desired results.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of medical imaging comprising:

(a) obtaining at a first temporal resolution a first medical image of a region of interest of a patient;

(b) obtaining at a second temporal resolution a second medical image of the region of interest, said second temporal resolution being lower than the first temporal resolution;

(c) registering the first and second medical images with one another such that common reference points in the first and second medical images coincide; and, (d) superimposing the first and second medical images over one another.

2. The method according to claim 1, wherein the first temporal resolution is such that a substantially instantaneous image is achieved.

3. The method according to claim 1, wherein the second temporal resolution is such that the second image is obtained over a period of time substantially equal to or greater than a period for a biological cycle of the patient.

4. The method according to claim 1, wherein the biological cycle is a cycle selected from the group consisting of the patient's respiratory cycle and the patient's cardiac cycle.

5. The method according to claim 1, wherein the second temporal resolution is such that the second image visualizes a range of motion of a selected mass of tissue.

6. The method according to claim 5, wherein the first temporal resolution is such that the first image visualizes the selected mass of tissue.

7. The method according to claim 6, further comprising:

coloring the selected mass of tissue visualized in the first image with a first color; and, coloring the range of motion visualized in the second image with a second color, said second color being different from the first color.

8. The method according to claim 1, wherein the superimposed first and second images visualize a shape and size of a selected mass of tissue and a range of motion experienced by the selected mass of tissue.

9. The method according to claim 1, further comprising:

planning a targeted treatment in the region of interest based on the superimposed first and second images.

10. The method according to claim 1, wherein the first and second images are three-dimensional images.

11. A medical imaging apparatus comprising:

a medical imager which produces image representations of a region of interest of a patient at two different temporal resolutions;

registration means for aligning with one another first and second image representations of the same region of interest obtained from the medical imager at different first and second temporal resolutions, respectively; and, combining means for superimposing aligned first and second image representations over one another.

12. The medical imaging apparatus of claim 11, further comprising:

a display for rendering in a human-viewable format the superimposed first and second image representations.

13. The medical imaging apparatus of claim 11, wherein the medical imager is selected from the group consisting of a CT scanner, an MRI scanner, a SPECT scanner, PET scanner, and a fluoroscope.

14. The medical imaging apparatus of claim 11, wherein the superimposed first and second image representations visualize a shape and size of a selected mass of tissue in the region of interest and a range of motion experienced by the selected mass of tissue.

15. The medical imaging apparatus of claim 14, further comprising:

a marking engine which selectively colors the selected mass visualized in the superimposed first and second image representations a first color, and selectively colors the range of motion visualized in the superimposed first and second image representations a second color different from the first color.

16. The medical imaging apparatus of claim 11, further comprising:

a treatment planning workstation which accesses the superimposed first and second image representations to carry out computer simulated treatments.

17. The medical imaging apparatus of claim 11, wherein the first temporal resolution is such that a substantially instantaneous image representation is achieved.

18. The medical imaging apparatus of claim 11, wherein the second temporal resolution is such that the second image representation is obtained over a period of time substantially equal to or greater than a period for a biological cycle of the patient.

19. The medical imaging apparatus of claim 18, wherein the biological cycle is a cycle selected from the group consisting of the patient's respiratory cycle and the patient's cardiac cycle.

20. The medical imaging apparatus of claim 11, wherein the second temporal resolution is such that the second image representation visualizes a range of motion of a selected mass of tissue in the region of interest.

* * * * *